(12) United States Patent
Marini et al.

(10) Patent No.: US 9,949,913 B2
(45) Date of Patent: Apr. 24, 2018

(54) LUMINATE FACE LOTION

(71) Applicant: Jan Marini Skin Research, San Jose, CA (US)

(72) Inventors: Jan Marini, San Jose, CA (US); Subhash J. Saxena, Ringoes, NJ (US)

(73) Assignee: Jan Marini Skin Research, San Jose, CA (US)

( * ) Notice: Subject to any disclaimer, the term of this patent is extended or adjusted under 35 U.S.C. 154(b) by 39 days.

(21) Appl. No.: 15/069,805

(22) Filed: Mar. 14, 2016

(65) Prior Publication Data

US 2017/0258697 A1   Sep. 14, 2017

(51) Int. Cl.

| A61K 8/64 | (2006.01) |
|---|---|
| A61K 8/34 | (2006.01) |
| A61K 8/35 | (2006.01) |
| A61K 8/49 | (2006.01) |
| A61K 8/60 | (2006.01) |
| A61K 8/63 | (2006.01) |
| A61Q 19/02 | (2006.01) |
| A61Q 19/08 | (2006.01) |

(52) U.S. Cl.
CPC .............. *A61K 8/64* (2013.01); *A61K 8/34* (2013.01); *A61K 8/342* (2013.01); *A61K 8/347* (2013.01); *A61K 8/35* (2013.01); *A61K 8/498* (2013.01); *A61K 8/602* (2013.01); *A61K 8/63* (2013.01); *A61Q 19/02* (2013.01); *A61Q 19/08* (2013.01); *A61K 2800/596* (2013.01)

(58) Field of Classification Search
None
See application file for complete search history.

(56) References Cited

U.S. PATENT DOCUMENTS

| 6,821,524 | B2 | 11/2004 | Marini | |
|---|---|---|---|---|
| 8,318,678 | B2 | 11/2012 | Marini | |
| 2003/0095959 | A1* | 5/2003 | Mayne | A61K 8/35 424/94.4 |
| 2006/0188559 | A1* | 8/2006 | Neis | A61K 8/14 424/450 |
| 2007/0196318 | A1 | 8/2007 | Marini | |
| 2009/0263513 | A1* | 10/2009 | Marini | A61K 8/347 424/729 |
| 2010/0055059 | A1* | 3/2010 | Criton | A61K 8/64 424/62 |
| 2010/0247693 | A1 | 9/2010 | Marini | |
| 2013/0189211 | A1 | 7/2013 | Marini | |
| 2014/0228291 | A1 | 8/2014 | Subhash et al. | |

FOREIGN PATENT DOCUMENTS

| EP | 1203579 A1 | 5/2002 |
|---|---|---|
| EP | 1369107 A1 | 12/2003 |
| EP | 1825845 A1 | 8/2007 |
| WO | 2009/148551 A1 | 12/2009 |

* cited by examiner

*Primary Examiner* — Robert A Wax
*Assistant Examiner* — William Craigo
(74) *Attorney, Agent, or Firm* — Pamela J. Sherwood; Bozicevic, Field & Francis LLP

(57) ABSTRACT

The present invention features novel cosmetic skin care compositions for improving the appearance of skin, particularly the reducing the appearance of age spots and discoloration.

4 Claims, 1 Drawing Sheet
(1 of 1 Drawing Sheet(s) Filed in Color)

LUMINATE FACE LOTION

BACKGROUND OF THE INVENTION

Researchers have examined aspects of human faces that affect perceptions of health, attractiveness, and age. Recently, several studies have focused on the contributions of skin color and texture to apparent facial health and attractiveness. The homogeneity and distribution of skin color across the face contributes to perceptions of health, age, and attractiveness of human faces. Ratings of facial attractiveness correlated with measures of skin color homogeneity, such that more homogeneous skin color distribution was more attractive. More homogeneous chromophore (melanin and hemoglobin) distribution across the skin also correlates positively with ratings of health, attractiveness, and youthfulness, while the facial color distribution of younger women is perceived as younger, healthier, and more attractive than that of older women.

The most visible signs of aging are sun damage, wrinkles and abnormal pigmentation; and virtually 100% of all adults show signs of pigment change associated with aging. Several studies show that abnormal pigmentation affects 75%-100% of adults 35 years or older. Further, increased contrast between the luminance of the facial features and the rest of the facial skin has been shown to enhance the attractiveness and femininity of female faces. Evidence suggests that skin color and texture themselves contribute to the attractiveness of faces independently of shape, and when color distribution across the whole face cannot be viewed.

Cosmetic products that improve skin tone, texture and luminosity are of great interest, and can provide a complement to skin care routines to combat pigmentation. A high consumer interest in lightening is shown by the continual release of new products with new technologies by nearly all major companies. In addition, growing and continuing negative sentiment toward the use of hydroquinone is prompting consumers and professionals to seek alternate viable solutions.

SUMMARY OF THE INVENTION

The present invention provides cosmetic formulations for improving the appearance of the skin, including the facial area. The compositions of the invention are designed for use as a lotion to lighten the appearance of discoloration and reduce the appearance of fine lines and wrinkles. The compositions of the present invention provide a broad range of lightening technologies to reduce undesirable pigmentation from a plurality of pathways with visible results as early as about 2 to about 4 weeks. A high concentration of retinol is provided to accelerate improvement in the appearance of discoloration and simultaneously target the appearance of fine lines and wrinkles.

According to the first aspect of the invention, there is provided a cosmetic composition comprising a specific and efficacious blend of agents, including skin brightening agents nonapeptide-1, tetrahydrodiferuloylmethane (colorless, non-staining tumeric), alpha-arbutin, hexylresorcinol, and dipotassium glycyrrhizate. Retinol and epigallocatechin gallate are provided, which aid in reducing the appearance of fine lines and wrinkles. Specific skin soothing agents include tetrahydrodiferuloylmethane, epigallocatechin gallate, and bisabolol.

In the second aspect of the invention, a method is provided for improving the appearance of the skin, in particular to improve skin tone, texture and luminosity, the method comprising applying topically a cosmetic lotion composition comprising an efficacious blend of nonapeptide-1, tetrahydrodiferuloylmethane, alpha-arbutin, hexylresorcinol, dipotassium glycyrrhizate, retinol, epigallocatechin gallate, and bisabolol.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1A:
FIGS. 1A and 1B show the results of use of Luminate face lotion. The lotion was applied twice daily for one month (A) and for 2 months (B). The results show a dramatic change in skin tone after regular use of the product.
Figure 1B:

Topical compositions are provided for improving the appearance of the skin, particularly in lightening and evening skin tone. The compositions of the invention include a cosmetically acceptable vehicle to act as a diluent, dispersant or carrier for the active agents, so as to facilitate distribution and uptake when the composition is applied as a skin lotion, which may be applied daily, twice daily, e.g. morning and night. Vehicles other than water can include liquid or solid emollients, solvents, humectants, thickeners and powders, including for example cyclic polysiloxanes. The cosmetically acceptable vehicle will usually form 5% to 99.9%, preferably from 25% to 80%, about 40% to 60%, by weight of the composition, and can, in the absence of other cosmetic adjuncts, form the balance of the composition.

The compositions may be in the form of an aqueous lotion. These compositions are formulated according to the usual techniques as are well known to this art. The compositions of the invention may further comprise cosmetically useful agents and excipients, e.g. glycerin, cetyl alcohol, capric triglyceride, glyceryl stearate, PEG-100 stearate, steareth-20, steareth-2, cyclopentasiloxane, phenoxyethanol, lecithin, tocopherol, aloe vera, etc. each at a concentration of from about 0.1% to about 10% by weight, usually from about 0.5% to about 5%, and may be present at a concentration of from about 0.5%, 1%, 2%, 3%, 4%, 5%, etc.

Components of the Cosmetic Compositions

The compositions of the invention comprise a specific blend of therapeutic agents.

Lightening agents in the formulation include nonapeptide-1, tetrahydrodiferuloylmethane (colorless, non-staining tumeric), alpha-arbutin, hexylresorcinol, and dipotassium glycyrrhizate.

Peptides, including but not limited to, di-, tri-, tetra-, and pentapeptides, as well as oligo-peptides of from about 3 to about 10 amino acids in length and derivatives thereof, comprising at least one lipid moiety, which moiety may be myristoyl, palmitoyl, etc., may be included in compositions of the present invention in amounts that are safe and effective. The formulation comprises an effective dose of one or more such acylated peptides, which peptides are active in remodeling of the skin.

Peptides of particular interest include biomimetic peptide antagonist of a melanocyte stimulating hormone, including specifically nonapeptide-1 (MELANOSTATINE®5), CA 7732-18-5. The peptide agents of the present invention are formulated at an effective concentration within the subject cosmetic compositions, meaning at a concentration that provides the intended benefit when applied topically. An effective concentration of peptide or peptide-like compounds is preferably in a range of at least about 0.0001% to about 0.01, usually about 0.0001% to about 0.0005%; and each peptide may be present at a concentration of about 0.0001 to 0.0002%.

Tetrahydrodiferuloylmethane (1,7-Bis(4-hydroxy-3-methoxyphenyl)-3,5-heptanedione-d6) is a colorless hydrogenated product derived from curcuminoids, which function as an antioxidant and lightening agent. The compound also inhibits the action of tyrosinase that participates in melanin formation. An effective concentration in compositions of the invention are preferably in a range of at least about 0.1% to about 1%, usually about 0.2% to about 0.5%, and may be provided at a concentration of about 0.2%.

Alpha-Arbutin (4-Hydroxyphenyl-α-D-glucopyranoside) is a functional active ingredient for skin lightening, CAS#84380-01-8. Alpha-Arbutin blocks epidermal melanin biosynthesis by inhibiting enzymatic oxidation of Tyrosine and Dopa. AlphaArbutin may be provided in the compositions of the invention at a concentration of from about 0.1% to about 5%, usually from about 0.5% to about 2.5%, and may be about 1% by weight.

Hexylresorcinol is a substituted phenol with skin lightening properties. It may be present in the composition at a concentration of from about 0.5 to about 2% by weight, usually from about 0.75% to about 1.25%, and may be present at a concentration of about 1%. Hexylresorcinol is known in the art and commercially available under CAS #136-77-6 from various suppliers.

Dipotassium glycyrrhizate may be present in the composition at a concentration of from about 0.5% to about 2.5% by weight, usually about 0.1% to about 1.5%, and may be present at about 1% by weight. Dipotassium glycyrrhizate is a licorice root extract with skin lightening properties. Dipotassium glycyrrhizate is known in the art and commercially available under CAS #68797-35-3 from various suppliers.

Retinol, CAS number 68-26-8, (2E,4E,6E,8E)-3,7-dimethyl-9-(2,6,6-trimethylcyclohex-1-enyl) nona-2,4,6,8-tetraen-1-ol, may be present at a concentration of from 0.5% to about 2.5%. Formulations with higher or lower concentrations of retinol are available, where a high dose may have from about 0.5% to about 1% retinol, for example at about 0.75%. A low dose formulation may have from about 0.1% to about 0.5% retinol, for example at around about 0.35%

Epigallocatechin gallate (CAS 989-51-5) is the ester of epigallocatechin and gallic acid, and is a type of catechin. It is found in high content in the dried leaves of tea. The present formulations contain a concentration that is useful in soothing the skin, as well as reducing the appearance of fine lines and wrinkles. It may be present in the formulation at a concentration of from about 0.5% to about 2.5% by weight, usually about 0.1% to about 1.5%, and may be present at about 1% by weight.

Alpha-Bisabolol ((R',R')-α,4-dimethyl-α-(4-methyl-3-pentenyl)cyclohex-3-ene-1-methanol, CAS Number 515-69-5/23089-26-1) is a skin soothing agent, that may be present in the composition at a concentration of from about from 0.05 to 0.5%, usually about 0.1-0.25%, and may be present at a concentration of about 0.1% by weight.

The compositions of the invention may optionally comprise other skin benefit materials. These include estradiol; progesterone; pregnanalone; coenzyme Q10; methylsolanomethane (MSM); copper peptide (copper extract); plankton extract (phytosome); kojic acid; broparoestrol; estrone; adrostenedione; androstanediols; hydroquinone; isoflavones, etc. The steroids will generally be present at a concentration of less than about 5% or about 10% of the total by weight of the composition, while the other skin benefit materials may be present at higher levels, for example as much as about 10 to about 15%.

The amounts of cosmetic or dermatological auxiliaries and additives and perfume to be used in each case can easily be determined by simple exploratory experiments by the person skilled in the art, depending on the nature of the product in question. Preferably the compositions of the invention are fragrance free and paraben-free.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The compositions of the invention include a cosmetically acceptable vehicle to act as a diluent, dispersant or carrier for the active agents, so as to facilitate distribution and uptake when the composition is applied as a lotion. Vehicles other than or in addition to water, triglycerides, glycerol, etc. can include liquid or solid emollients, solvents, humectants, thickeners and powders. The cosmetically acceptable vehicle will usually form 5% to 99.9%, preferably from 25% to 80%, about 40% to 60%, by weight of the composition, and can, in the absence of other cosmetic adjuncts, form the balance of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Accordingly, a composition of the invention comprises a lotion with skin lightening agents, retinol, epigallocatechin gallate and bisabolol in an emulsion suitable for administration as a lotion. Furthermore, a composition of the invention may include additional agents or additives that are not in themselves active agents but play a role in promoting the usefulness or effectiveness of an active agent.

Compositions of the invention may be applied to any subject and used to treat a variety of conditions, particularly for the reducing the appearance of spots and discoloration, reducing the appearance of redness, brightening skin and reducing the appearance of fine lines and wrinkles. A typical composition of the invention is formulated as a lotion, which may be applied topically once or twice daily.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the neck, the face, etc.

The cosmetic composition of the invention can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

Example 1

Example 1 illustrates a topical composition according to the present invention. The composition can be processed in conventional manner and is suitable for cosmetic use. In particular the compositions are suitable for application to a site of interest for the treatment of a variety of skin conditions.

Marini Luminate Lotion

| CAS number | Name | Final concentration |
|---|---|---|
| 7732-18-5 | Nonapeptide-1 | 0.0001-0.001% |
| 36062-04-1 | Tetrahydrodiferuloymethane | 0.1-0.5% |
| 84380-01-8 | Alpha-Arbutin | 0.5-2.5% |
| 136-77-6 | 4-Hexylresorcinol | 0.5-2.5% |
| 68797-35-3 | Dipotassium Glycyrrhizate | 0.5-2.5% |
| 68-26-8 | Retinol | 0.5-1.25% |
| 989-51-5 | Epigallocatechin Gallate | 0.5-2.5% |
| 515-69-5 | Alpha-Bisabolol | 0.05-0.5% |

Additional ingredients can be included to provide a cosmetically acceptable vehicle and to bring the volume to 100%, comprising one or more of water, cyclic polysiloxanes, glycerin, caprylic/capric triglyceride, glyceryl stearate, cetyl alcohol, propanediol, C12-15 alkyl benzoate, sclerotium gum, beta vulgaris (beet) root extract, butylene glycol, caesalpinia spinosa gum, tocopheryl acetate, hexylene glycol, lecithin, PEG-100 stearate, phenoxyethanol, sodium acrylates copolymer, sorbitan stearate, xanthan gum.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application comprising:

from 0.0001 to 0.001% by weight nonapeptide-1; from 0.1 to 0.5% tetrahydrodiferuloylmethane; from 0.5 to 2.5% alpha arbutin; from 0.5 to 2.5% 4-hexylresorcinol; from 0.5% to 1% retinol; from 0.5 to 2.5% epigallocatechin gallate; from 0.05% to 0.5% alpha-bisabolol; and from 0.5 to 2.5% dipotassium glycyrrhizate; and a cosmetically acceptable vehicle.

2. The composition of claim 1, formulated as a lotion.

3. A cosmetic composition for topical application comprising:

from 0.0001 to 0.001% by weight nonapeptide-1; from 0.1 to 0.5% tetrahydrodiferuloylmethane; from 0.5 to 2.5% alpha arbutin; from 0.5 to 2.5% 4-hexylresorcinol; from 0.5% to 1% retinol; from 0.5 to 2.5% epigallocatechin gallate; from 0.05% to 0.5% alpha-bisabolol; from 0.5 to 2.5% dipotassium glycyrrhizate; in the absence of hydroquinone; and a cosmetically acceptable vehicle.

4. A method of reducing undesirable pigmentation of the skin, comprising:

administering topically to the skin a cosmetic formulation of claim 1.

* * * * *